United States Patent [19]

Nagaoka et al.

[11] 4,039,527
[45] Aug. 2, 1977

[54] UNSYMMETRICAL AZONITRILES

[75] Inventors: Joji Nagaoka, Tokyo; Kazuhiko Yamashita, Wako; Nobuaki Minamii; Tsutomu Miyagawa, both of Kawagoe; Masahiko Sugano, Sakato, all of Japan

[73] Assignee: Wako Pure Chemical Industries, Ltd., Osaka, Japan

[21] Appl. No.: 513,846

[22] Filed: Oct. 10, 1974

[51] Int. Cl.² .......................................... C07C 107/02
[52] U.S. Cl. ............................. 260/192; 260/465.5 R; 526/218; 526/219
[58] Field of Search ........................................ 260/192

[56] References Cited

U.S. PATENT DOCUMENTS

| | | | |
|---|---|---|---|
| 2,469,358 | 5/1949 | Alderson et al. | 260/144 X |
| 2,492,763 | 12/1949 | Pinkey | 260/192 |
| 2,515,628 | 7/1950 | Castle | 260/192 |
| 2,520,339 | 8/1950 | Robertson | 260/192 X |
| 2,586,995 | 2/1952 | Robertson | 260/192 |
| 2,666,758 | 1/1954 | Johnson et al. | 260/192 |
| 2,877,102 | 3/1959 | Levesque | 44/57 |
| 3,192,196 | 6/1965 | Vidal et al. | 260/192 |
| 3,775,395 | 11/1973 | Koyanagi et al. | 260/192 |
| 3,783,148 | 1/1974 | Fuchs et al. | 260/192 |
| 3,876,622 | 4/1975 | Motokawa | 260/192 X |

FOREIGN PATENT DOCUMENTS

| | | | |
|---|---|---|---|
| 1,224,084 | 6/1960 | France | 260/192 |
| 46-15495 | 4/1971 | Japan | 260/192 |
| 46-15496 | 4/1971 | Japan | 260/192 |

Primary Examiner—Charles F. Warren
Attorney, Agent, or Firm—Armstrong, Nikaido & Marmelstein

[57] ABSTRACT

Unsymmetrical azonitriles of the formula,

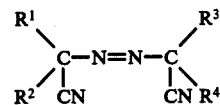

wherein $R^1$, $R^2$, $R^3$ and $R^4$ are independently straight- or branched-chain alkyl having 1 to 7 carbon atoms or alkoxy substituted straight- or branched-chain alkyl having 2 to 11 carbon atoms but at least one of $R^1$ and $R^2$ and at least one of $R^3$ and $R^4$ must be different, have good efficiency as initiator for polymerizations or copolymerizations of vinyl monomers. These unsymmetrical azonitriles can be prepared by oxidizing a corresponding unsymmetrical hydrazo compound.

7 Claims, 3 Drawing Figures

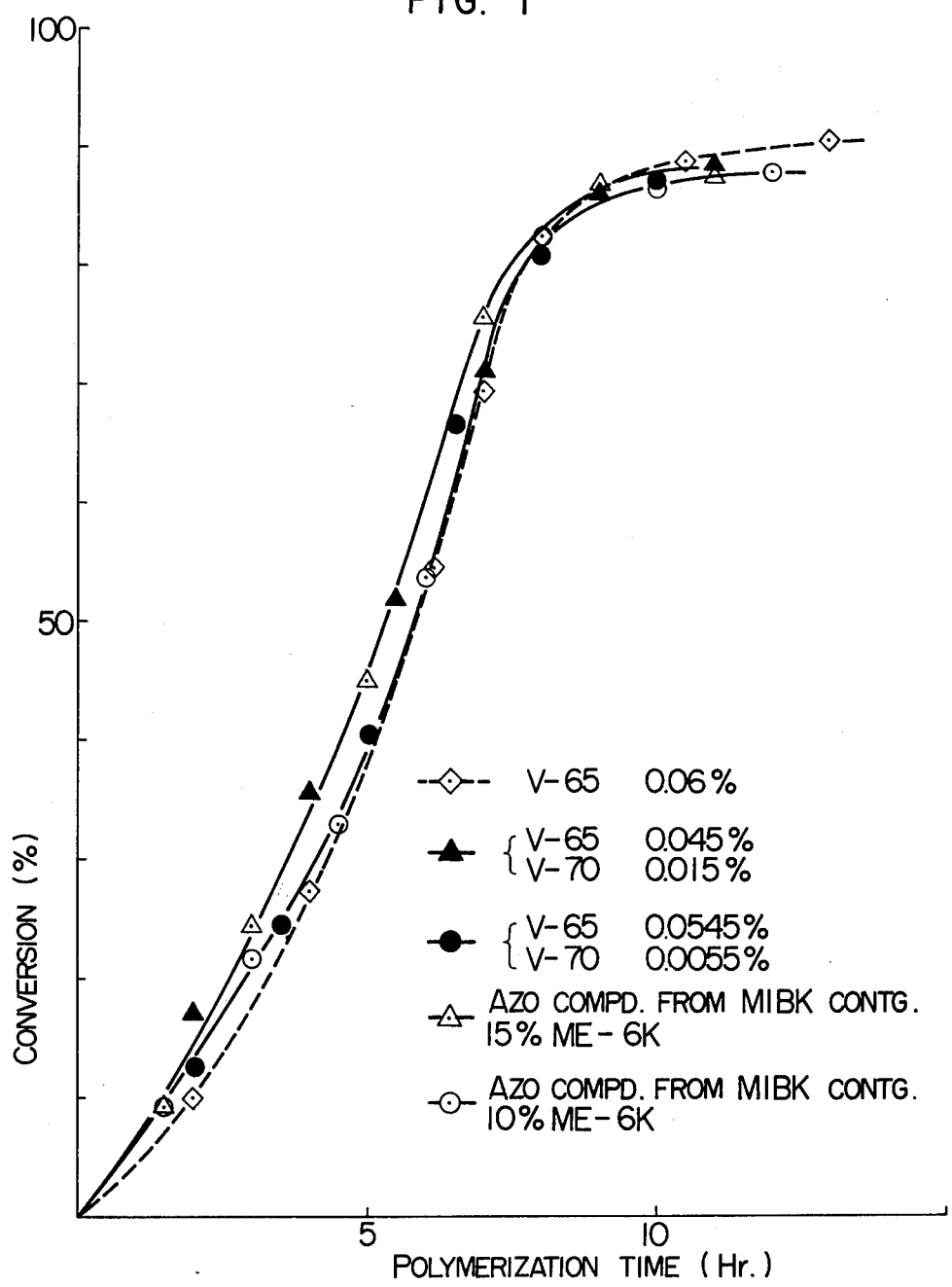

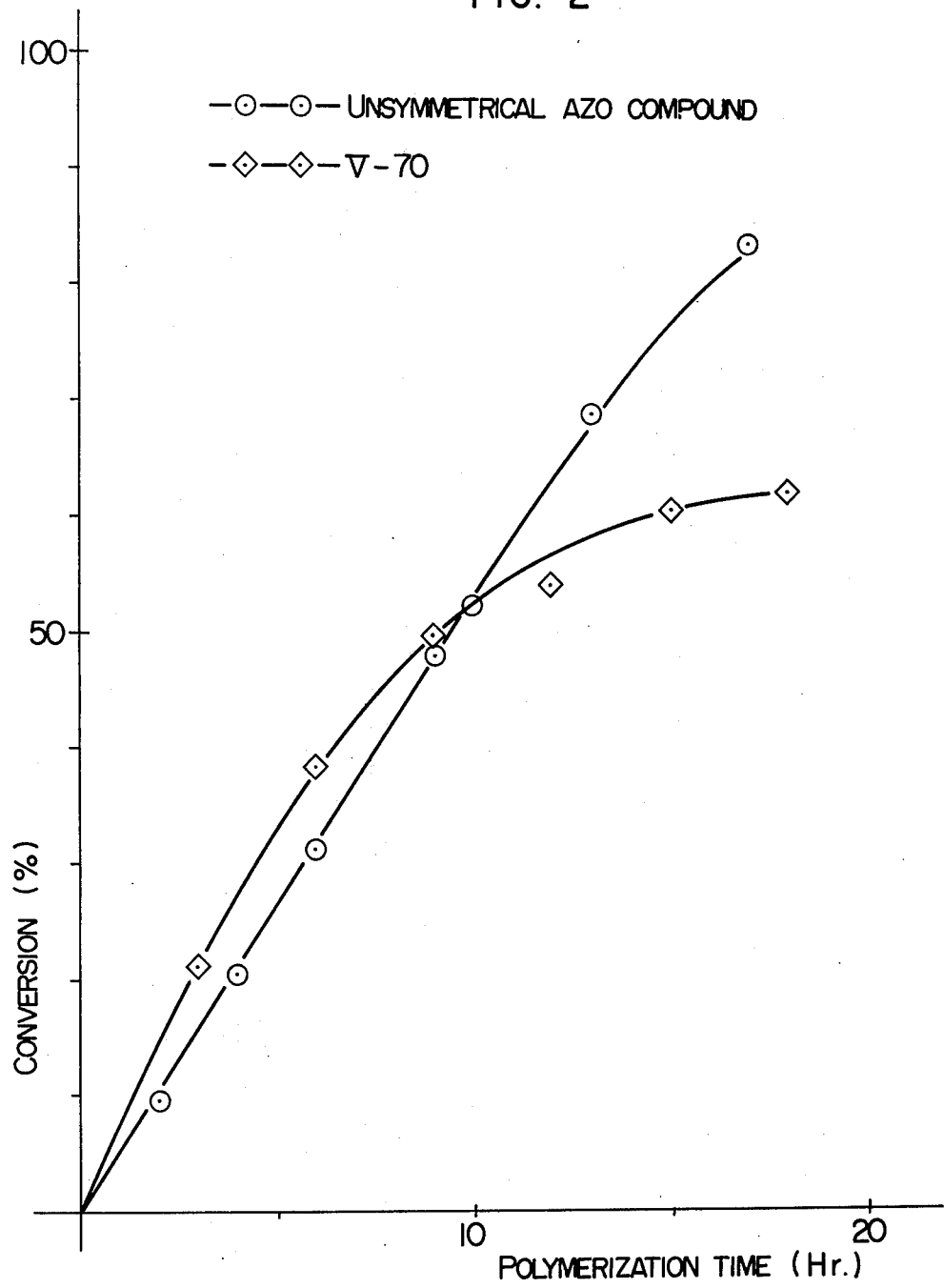

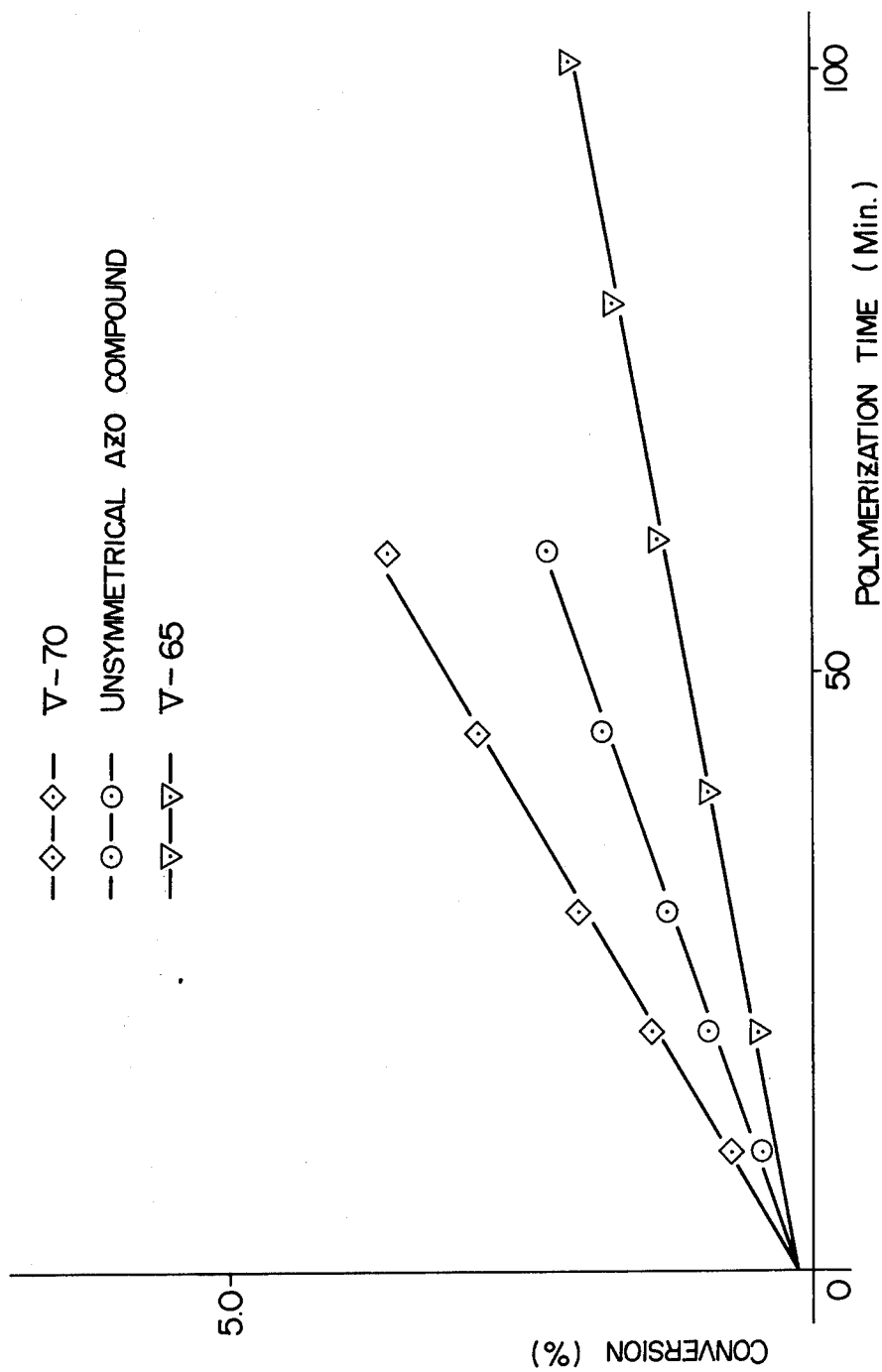

UNSYMMETRICAL AZONITRILES

This invention relates to novel unsymmetrical azonitriles having different substituents on both sides of the azo group and a process for producing the same.

The unsymmetrical azonitriles of the present invention are useful as initiators for polymerizations because of their good efficiency. The term "good efficiency" used in this invention means ability to produce not only great decomposition rate and short half-life period but also other various effects such as easiness in temperature control, easiness in catalyst addition, no yield point on polymerization curve and the like in the desired polymerization scale.

Heretofore various azo compounds have been used as polymerization initiators depending on the kind of monomers and physical properties of the desired polymers, but they are inadequate in efficiency. Thus polymerization initiators having better efficiency have long been desired industrially. Symmetrical azonitriles have also been used as polymerization initiators but their kinds are very limited since their starting materials are very limited industrially. Therefore it has been very difficult to obtain symmetrical azonitriles having suitable activity and good efficiency for some kinds of polymerization. In order to obtain suitable activity, co-use of an initiator having high-temperature activity and another initiator having low-temperature activity has been proposed but this method has various defects such as decrease in polymerization rate during polymerization due to transfer of initiator efficiency, decrease in physical properties of polymers obtained, and the like.

It is an object of the present invention to provide novel unsymmetrical azonitriles. It is a further object of the present invention to provide unsymmetrical azonitriles useful as polymerization initiators having various activities and good efficiency. It is another object of the present invention to provide a process for preparing such novel unsymmetrical azonitriles. It is a still further object of the present invention to provide a composition containing an unsymmetrical azonitrile and simultaneously by-produced symmetrical azonitriles. Further objects and advantages of the present invention will be apparent to one skilled in the art from the accompanying disclosure and discussion.

The present invention provides an unsymmetrical azonitrile of the formula, $$\begin{array}{c} R^1 \\ \diagdown \\ R^2 \diagup \end{array} C - N = N - C \begin{array}{c} R^3 \\ \diagup \\ \diagdown R^4 \end{array} \qquad (I)$$
$$\phantom{xxxxx} | \phantom{xxxxxxxxx} | $$
$$\phantom{xxxxx} CN \phantom{xxxxxxx} CN$$

wherein $R^1$, $R^2$, $R^3$ and $R^4$ are independently straight- or branched-chain alkyl having 1 to 7 carbon atoms, preferably 1 to 5 carbon atoms or alkoxy substituted straight- or branched-chain alkyl having 2 to 11 carbon atoms provided that at least one of $R^1$ and $R^2$ and at least one of $R^3$ and $R^4$ must be different.

In the formula (I), the straight- or branched-chain alkyl having 1 to 7 carbon atoms includes, for example, methyl, ethyl, propyl, isopropyl, n-butyl, isobutyl, t-butyl, isoamyl, n-amyl, dimethylpropyl, 2-methylbutyl, n-hexyl and n-heptyl. The term "alkoxy substituted straight- or branched-chain alkyl" means that at least one hydrogen in said alkyl having 1 to 7 carbon atoms is substituted by at least one alkoxy having 1 to 4 carbon atoms. The term "alkoxy" includes, for example, methoxy, ethoxy, propoxy and butoxy.

Preferred examples of the azonitriles of the formula (I) are as follows:

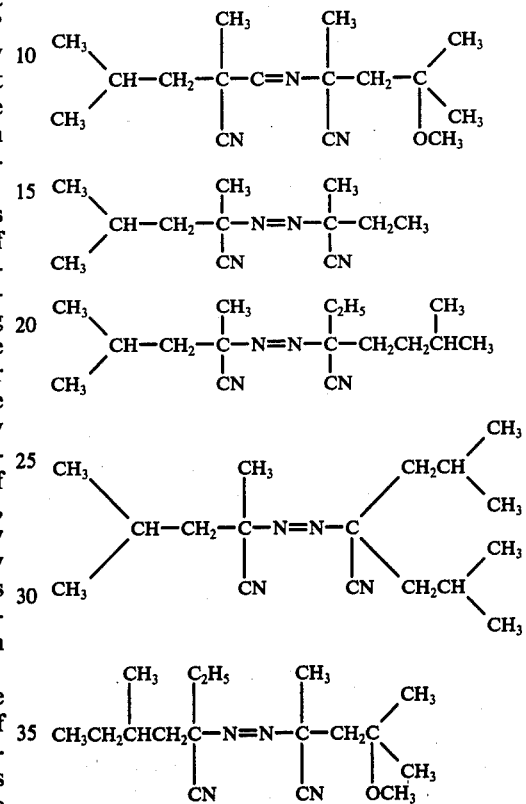

The unsymmetrical azonitriles of the formula (I) have good efficiency as polymerization initiators. Further the unsymmetrical azonitriles of the formula (I) are liquid at room temperature contrary to known azo polymerization initiators which are solid in most cases. This makes it possible to carry out polymerizations or copolymerizations more efficiently since the unsymmetrical azonitriles of the present invention have many advantages in that they are not solidified during storage, it is easy to weigh and charge them for polymerization, they are easily dissolved in or admixed with various monomers and the like.

Temperatures employed for thermal decomposition of unsymmetrical azonitriles of the present invention depend on thermal stabilities (half-life periods) of the azonitriles having various substituents. Some examples of the temperature at which typical unsymmetrical azonitriles of the present invention are reduced to one-half their initial weights for 10 hours are listed in Table 1.

Table 1

| Unsymmetrical azonitriles | $\tau_{\frac{1}{2}}$ (10 hrs.) |
|---|---|
| 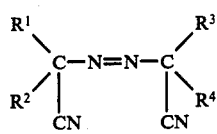 | 39° C |

Table 1-continued

| Unsymmetrical azonitriles | $\tau\frac{1}{2}$ (10 hrs.) |
|---|---|
| 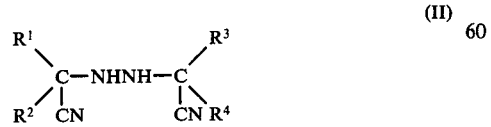 | 59° C |
| CH₃—CHCH₂—C(CN)(CH₃)—N=N—C(CN)(CH₃)—CH₂CH₃ with CH₃ branches | |
| CH₃—CHCH₂—C(CN)(CH₃)—N=N—C(C₂H₅)(CN)—CH₂CH₂CHCH₃ with CH₃ branches | 48° C |
| CH₃—CHCH₂—C(CN)(CH₃)—N=N—C(CN)(CH₃)—CH₂C(CH₃)(OCH₃) with CH₃ branches | 40° C |

When the unsymmetrical azonitriles of the present invention are used as polymerization initiators, they may be used alone or as a mixture thereof or a mixture of at least one of them and at least one of known azo compounds or known peroxides.

The unsymmetrical azonitriles of the present invention can be used for radical polymerizations or copolymerizations of vinyl monomers like conventional azo initiators. Examples of vinyl monomers are vinyl chloride, butadiene, styrene, acrylic ester, methacrylic ester, acrylonitrile, vinylidene halide, vinyl acetate, acrylamide, acrylic acid, methacrylic acid, vinylpyridine and the like. These vinyl monomers may be copolymerized with other polymeriable organic compounds having at least one ethylenic bond such as maleic acid, fumaric acid, crotonic acid, etc. efficiently using the unsymmetrical azonitriles.

Temperatures of polymerizations or copolymerizations may be varied with the kinds of initiators and monomers employed but usually are 20° to 150° C. It is preferable to carry out polymerization or copolymerization under an atmosphere of inert gas. Any conventional methods may be used for polymerizations or copolymerizations using the unsymmetrical azonitriles of the present invention.

The unsymmetrical azonitriles of the formula (I) can be prepared by oxidizing an unsymmetrical hydrazo compound of the formula, $$\underset{R^2}{\overset{R^1}{\diagdown}}\underset{CN}{\overset{|}{C}}-NHNH-\underset{CN}{\overset{|}{\underset{|}{C}}}\underset{R^4}{\overset{R^3}{\diagup}} \tag{II}$$

wherein R¹, R², R³ and R⁴ are as defined above. The oxidation can be carried out in the absence of a solvent, or in water or in an organic solvent using an oxidizing agent such as halogen, an alkali metal salt of hypohalite, an alkaline earth metal salt, hydrogen peroxide, and the like. The hydrazo compound of the formula (II) may be oxidized by oxygen in the presence of a metal catalyst such as cupric chloride. The oxidizing agent may be used in excess of the theoretical amount, or large in excess. As the organic solvent, there may be used methanol, ethanol, propanol, butanol, acetonitrile, dioxane, tetrahydrofuran, dimethylformamide, dichloromethane, chloroform, carbon tetrachloride, dichloroethane, ethyl acetate, benzene, toluene, etc. The oxidation reaction can be carried out at a temperature of −40° to +30° C.

The unsymmetrical hydrazo compound of the formula (II) can be prepared by various methods.

One method for preparing the unsymmetrical hydrazo compound of the formula (II) comprises reacting two different kinds of ketones with hydrazine with heating to give a ketazine and adding hydrogen cyanide to the ketazine or reacting two different kinds of ketones, hydrazine and hydrogen cyanide simultaneously as shown in the equation (1):

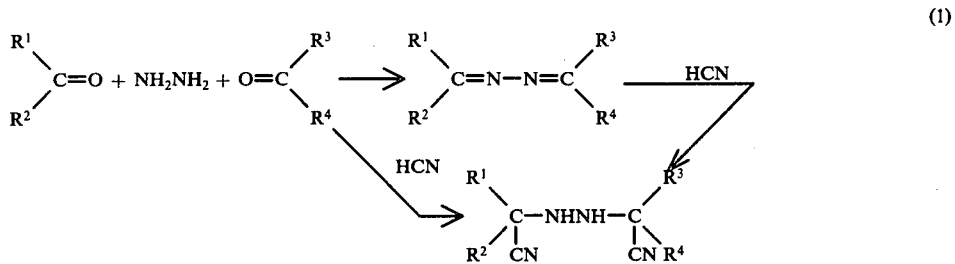

(1)

In the above equation (1), R¹, R², R³ and R⁴ are as defined above. The reaction to form the ketazine can be carried out at a temperature of 0° − 130° C, preferably 10° − 110° C. The addition of hydrogen cyanide can be carried out at 0° − 100° C, preferably 10° − 40° C. The ratio of two ketones to hydrazine can be varied depending on the reactivities of the ketones. The reaction can be carried out in the absence of a solvent or in water or in an organic solvent such as methanol, ethanol, propanol, acetonitrile, dioxane, tetrahydrofuran, in a homogeneous system or in a heterogeneous system.

Another method for preparing the unsymmetrical hydrazo compound of the formula (II) comprises reacting hydrazine with two different cyanohydrines, which are prepared by reacting ketones with hydrogen cyanide respectively, as shown in the equation (2):

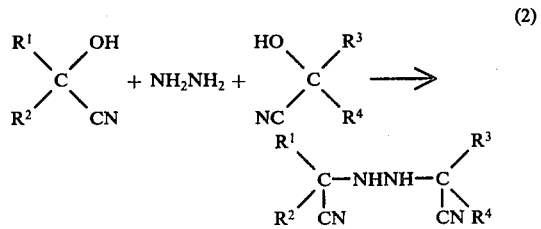

(2)

In the above equation (2), R¹, R², R³ and R⁴ are as defined above. The reaction can be carried out at a temperature of 0° − 100° C in the absence of a solvent or in water or in an organic solvent such as methanol, ethanol, propanol, acetonitrile, dioxane, tetrahydrofuran in a homogeneous system or in a heterogeneous system. The ratio of two cyanohydrins to hydrazine can be varied depending on the reactivities of the cyanohydrins.

A further method for preparing the unsymmetrical hydrazon compound of the formula (II) comprises reacting a ketone with hydrazine to give a hydrazone, reacting said hydrazone with a different kind of ketone to give a ketazine, and adding hydrogen cyanide to said ketazine, or adding hydrogen cyanide to said hydrazone and reacting the resulting compound with a different kind of ketone and successively with hydrogen cyanide, as shown in the equation (3):

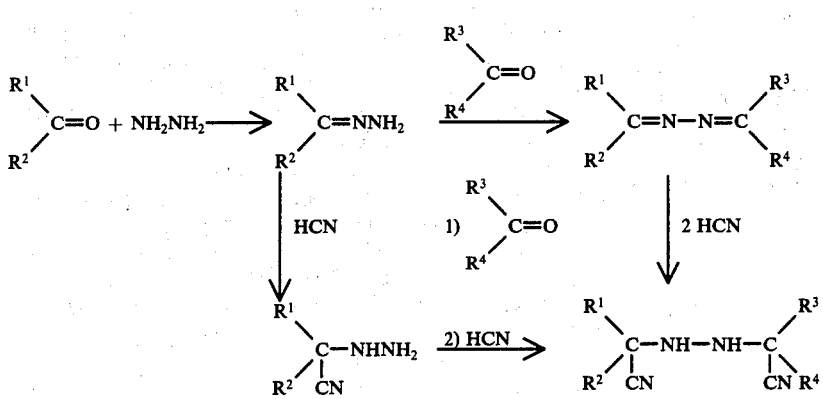

(3)

In the above equation (3), $R^1$, $R^2$, $R^3$ and $R^4$ are as defined above. The reactions to form the ketazine can be carried out at a temperature of 0° – 130° C, preferably 10° – 110° C in the absence of a solvent or in water or in an organic solvent such as methanol, ethanol, propanol, acetonitrile, dioxane, tetrahydrofuran in a homogeneous system or in a heterogeneous system. The addition of hydrogen cyanide can be carried out at 0° – 100° C, preferably 10° – 40° C. In the reaction of a ketone and hydrazine to prepare a hydrazone, most preferable reaction conditions are employed depending on the reactivity of the ketone with hydrazine, and it is preferable to add a weak basic salt such as barium oxide, magnesium oxide, etc. to the reaction system in order to increase the yield.

Ketazines or cyanoalkylhydrazines from which by-produced symmetrical compounds are removed by a conventional distillation may be used for synthesizing pure unsymmetrical hydrazo compounds of the formula (II).

On the other hand, a mixture containing an unsymmetrical hydrazo compound of the formula (II) and by-produced symmetrical compounds can be oxidized to produce a mixture containing an unsymmetrical azonitrile of the formula (I) and symmetrical azonitriles. Said azonitrile mixture also has good efficiency as polymerization initiator. The unsymmetrical azonitrile in said mixture can be identified by, for example, thinlayer chromatography. The proportion of the unsymmetrical azonitrile in said mixture can be determined by measuring the decomposed products using gas chromatographical analysis. That is, since each azonitrile in said mixture has a different decomposition point, the proportion of each azonitrile in said mixture can be determined by measuring the ratio of decomposed products derived from each azonitrile by gradually increasing decomposition temperature.

The unsymmetrical azonitrile of the formula (I) or a mixture of the unsymmetrical azonitrile of the formula (I) and simultaneously by-produced symmetrical azonitriles has various desirable effects which cannot be expected for known symmetrical azonitriles.

One example of said various desirable effects can be seen in suspension polymerization of vinyl chloride. According to a known process, a polyvinyl chloride having a desirable polymerization degree for general purpose is obtained by polymerization at a certain constant temperature. In order to suppress gel effect and to carry out the polymerization efficiently at a certain constant temperature, an initiator having low-temperature activity and another initiator having high-temperature activity are used in combination so as to give continuous intermediate activity of the two initiators for polymerization rate, cooling capacity of a resin kettle being taken into consideration. But a fatal defect of this initiator system is that in an intermediate stage of the polymerization wherein the migration of initiation effect from the low-temperature active initiator to the high-temperature active initiator takes place, there appears catenary decrease of polymerization rate, which brings about various undesirable troubles such as elongation of polymerization time, nonuniformity of articles produced, fish eyes in film or sheet, etc.

On the contrary, when 2-(1-cyano-1,3-dimethylbutylazo)-4methoxy-2,4-dimethyl-valeronitrile, an unsymmetrical azonitrile of the present invention, or a mixture of said unsymmetrical azonitrile and simultaneously by-produced symmetrical azonitriles is used in the suspension polymerization of vinyl chloride, it is possible to carry out the polymerization continuously and uniformly, without gel effect and without catenary decrease of polymerization rate as mentioned above and to obtain porous polyvinyl chloride having narrow molecular-weight distribution and having no undesirable troubles such as coloration, fish eyes, etc.

Further, since the unsymmetrical azonitriles of the present invention have various activity depending on the kind of substituents, broader polymerization temperature can be employed than conventional processes using symmetrical azonitriles and instead of conventional co-use of a low-temperature active initiator and a high-temperature active initiator a suitable unsymmetrical azonitrile of the present invention can be used depending on the kind of monomer to be polymerized.

The following examples are presented to further illustrate the present invention. In these examples, the parts or percentages are by weight unless otherwise indicated.

EXAMPLE 1

A mixture of 30 parts of methyl isobutyl ketone and 13 parts of 4-methoxy-4-methyl-2-pentanone and 13 parts of 80% hydrazine hydrate were refluxed for 3 hours. The resulting oil layer was dispensed, washed with water and distilled under reduced pressure to give 20 parts of the fraction of 119° – 139° C/18 mmHg. After dissolving 20 parts of the fraction in 30 parts of methanol, 10 parts of hydrogen cyanide was introduced thereinto at 20° C and the resulting mixture was stirred for 20 hours. Then 3 parts of hydrochloric acid was added to the reaction mixture and 10 parts of chlorine was introduced thereinto and stirring was continued for additional 1 hour to give 20 parts of 2-(1-cyano-1,3-dimethyl-butylazo)-4-methoxy-2,4-dimethyl-valeronitrile. The product was pale yellow oil having a decomposition point of 52° C, UVλmax 346 nm, $\tau_{\frac{1}{2}}$(10 hours) being 40° C. The result of elementary analysis for $C_{15}H_{26}N_4O = 278.45$ was as follows:

|            | C (%) | H (%) | N (%) |
|------------|-------|-------|-------|
| Calculated | 64.69 | 9.43  | 20.13 |
| Found      | 64.32 | 9.22  | 20.01 |

EXAMPLE 2

A mixture of 30 parts of methyl isobutyl ketone and 8.6 parts of 80% hydrazine hydrate was refluxed for 1 hour. The resulting oil layer was dispensed and distilled under reduced pressure to give 25 parts of the fraction of 39° – 43° C/5 mmHg. The fraction was mixed with 14 parts of methyl ethyl ketone and the mixture was refluxed for 2 hours. The resulting oil layer was dispensed, washed with water and distilled under reduced pressure to give 15 parts of the fraction of 89.5° – 95° C/18 mmHg. After dissolving 15 parts of the fraction in 20 parts of acetonitrile, 6.5 parts of hydrogen cyanide was introduced thereinto at 20° C and the resulting mixture was stirred for 20 hours. Then 2 parts of hydrochloric acid was added to the reaction mixture and 6.5 parts of chlorine was introduced thereinto and stirring was continued for additional 1 hour to give 13 parts of 2-(1-methyl-1-cyano-3-methyl-butylazo)-2-methyl-butyronitrile. The product was pale yellow oil having a decomposition point of 88° C, UVλmax 348 nm, $\tau_{1/2}$(10 hours) being 59° C. The result of elementary analysis for $C_{12}H_{20}N_4 = 220.36$ was as follows:

|            | C (%) | H (%) | N (%) |
|------------|-------|-------|-------|
| Calculated | 65.40 | 9.17  | 25.43 |
| Found      | 64.98 | 9.08  | 25.94 |

EXAMPLE 3

A mixture of 40 parts of methyl isobutyl ketone and 50 parts of ethyl isoamyl ketone and 40 parts of 80% hydrazine hydrate were refluxed for 3 hours. Using a procedure similar to that described in Example 1, 25 parts of ketazine having a boiling point of 137° – 145° C/19 mmHg was obtained. After the addition of hydrogen cyanide and oxidation as described in Example 1, there was obtained 20 parts of 2-(1-methyl-1-cyano-pentylazo)-2-ethyl-4-methyl-hexylonitrile. The product was yellow oil having a decomposition point of 40° C, UVλmax 348 nm, $\tau_{1/2}$(10 hours) being 48° C. The result of elementary analysis for $C_{16}H_{28}N_4 = 276.48$ was as follows:

|            | C (%) | H (%) | N (%) |
|------------|-------|-------|-------|
| Calculated | 69.50 | 10.23 | 20.27 |
| Found      | 69.23 | 9.88  | 20.89 |

EXAMPLE 4

A mixture of 30 parts of methyl isobutyl ketone and 13 parts of 4-methoxy-4-methyl-2-pentanone and 26 parts of 80% hydrazine hydrate were refluxed for 2 hours. The resulting oil layer was dispensed and washed with water to give 60 parts of a mixture of ketazines. To the mixture of ketazines, 22 parts of hydrogen cyanide was added and the reaction was carried out at 20° C for 4 days. Into the reaction mixture, 20 parts of chlorine was introduced with cooling to give 45 parts of a mixture of unsymmetrical and symmetrical azonitriles. From the result of thin-layer chromatographic analysis using chloroform as a developer, the resulting mixture contained 2,2′-azobis(2,4-dimethyl-valeronitrile) ($R_f = 0.70$), 2,2′-azobis(4-methoxy-2,4-dimethyl-valeronitrile) ($R_f = 0.45$) and 2-(1-cyano-1,3-dimethyl-butylazo)-4-methoxy-2,4-dimethyl-valeronitrile ($R_f = 0.60$). By gas chromatographic analysis, the amounts of these azonitriles were 5.8 parts of 2,2′-azobis(2,4-dimethyl-valeronitrile), 1.3 parts of 2,2′-azobis(4-methoxy-2,4-dimethyl-valeronitrile) and 2.9 parts of 2-(1-cyano-1,3-dimethylbutylazo)-4-methoxy-2,4-dimethyl-valeronitrile.

EXAMPLE 5

Efficiency of the unsymmetrical azonitriles of the present invention as initiator was measured in the polymerization of vinyl chloride at 50° C.

In a pressure bottle, 100 parts of water, 53 parts of vinyl chloride, 0.06 part of polyvinyl alcohol (Gosenol GH-20, Nippon Synthetic Chemical Industry Co., Ltd.) and 0.06% of an initiator as listed below based on the weight of the monomer were placed and the polymerization was carried out. The relation between conversion and polymerization time for each initiator was shown in FIG. 1. For comparison, conventional symmetrical azonitriles were also used and plotted in FIG. 1. The used initiators were as follows:

A mixture of 2-(1-cyano-1,3-dimethyl-butylazo)-4-methoxy-2,4-dimethyl-valeronitrile and simultaneously by-produced symmetrical azonitriles prepared from methyl isobutyl ketone (MIBK) and 4-methoxy-4-methyl-2-pentanone (ME-6K)(referred to as AZO COMPD. FROM MIBK CONTG. 10% or 15% ME-6K)

V-65: 2,2′-Azobis(2,4-dimethyl-valeronitrile)

V-70: 2,2′-Azobis(4-methoxy-2,4-dimethylvaleronitrile).

As is clear from FIG. 1, the mixtures containing unsymmetrical azonitriles have quite different activities comparing with the symmetrical azonitrile or the mixtures containing only symmetrical azonitriles in the same proportions.

EXAMPLE 6

To 10 parts of vinyl acetate and 10 parts of methanol, 0.04 part of the initiator as listed in Table 2 was added and the polymerization was carried out under nitrogen at 58° C. Conversion with the lapse of time was as listed in Table 2. For comparison, the case when a conventional symmetrical azonitrile was used was also listed in Table 2.

Table 2

| Initiator | Polymerization time (hours) | Conversion (%) |
|---|---|---|
| CH₃—C(C₂H₅)(CN)—N=N—C(CH₃)(CN)—CH₂—CH(CH₃)₂ | 1<br>2<br>4<br>6 | 27<br>45<br>68<br>78 |
| CH₃—CH₂—CH(CH₃)—CH₂—C(C₂H₅)(CN)—N=N—C(CH₃)(CN)—CH₂—CH(CH₃)₂ | 1<br>2<br>4<br>6 | 37<br>60<br>76<br>84 |
| (Comparison)<br>(CH₃)₂CH—CH₂—C(CH₃)(CN)—N=N—C(CH₃)(CN)—CH₂—CH(CH₃)₂ | 1<br>2<br>4<br>6 | 35<br>58<br>75<br>82 |

EXAMPLE 7

To 5 parts of acrylonitrile, 0.1 part of sodium allylsulfonate, and 27 parts of dimethyl sulfoxide, 0.06 part of the initiator as listed in Table 3 was added and the polymerization was carried out under nitrogen at 40° C. Conversion with the lapse of time was as listed in Table 3. For comparison, the case when a conventional symmetrical azonitrile was used was also listed in Table 3.

| Initiator | Polymerization time (hours) | Conversion (%) |
|---|---|---|
| (CH₃)₂CH—CH₂—C(CH₃)(CN)—N=N—C(CH₃)(CN)—C₂H₅ | 2<br>4<br>6<br>10 | 15<br>31<br>44<br>66 |
| (CH₃)₂CH—CH₂—C(CH₃)(CN)—N=N—C(CH₃)(CN)—CH₂—C(OCH₃)(CH₃)—CH₃ | 2<br>4<br>6<br>10 | 35<br>61<br>79<br>94 |
| (Comparison)<br>(CH₃)₂CH—CH₂—C(CH₃)(CN)—N=N—C(CH₃)(CN)—CH₂—CH(CH₃)₂ | 2<br>4<br>6<br>10 | 25<br>49<br>72<br>88 |

EXAMPLE 8

Efficiency of the unsymmetrical azonitrile of the present invention as initiator was measured in the polymerization of vinyl chloride at 45° C.

In a pressure bottle, 100 parts of water, 53 parts of vinyl chloride, 0.06 part of polyvinyl alcohol (Gosenol GH-20, Nippon Synthetic Chemical Industry Co., Ltd.) and 0.03% of 2-(1-cyano-1,3-dimethyl-butylazo)-4-methoxy-2,4-dimethyl-valeronitrile based on the weight of the monomer were placed and the polymerization was carried out. The relation between conversion and polymerization time was shown in FIG. 2. For comparison, a conventional symmetrical azonitrile, 2,2'-azobis(4-methoxy-2,4-dimethyl-valeronitrile) (V-70), was also used and plotted in FIG. 2.

As is clear from FIG. 2, when the symmetrical azonitrile is used, activity for polymerization decreases during the polymerization. On the other hand, when the unsymmetrical azonitrile of the present invention is used, constant polymerization rate with remarkably high efficiency without gel effect can be obtained.

EXAMPLE 9

In a pressure bottle, styrene, which contained 3 × 10⁻³ mole/l. of 2-(1-cyano-1,3-dimethyl-butylazo)-4-methoxy-2,4-dimethyl-valeronitrile was placed and bulk polymerization of styrene was carried out under nitrogen at 45° C. The relation between conversion and polymerization time was shown in FIG. 3. For comparison, 2,2'-azobis(2,4-dimethyl-valeronitrile) (V-65) and 2,2'-azobis(4-methoxy-2,4-dimethyl-valeronitrile) (V-70) were also used as initiator and plotted in FIG. 3.

What is claimed is:

1. An unsymmetrical azonitrile of the formula

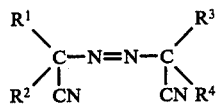

wherein R¹, R², R³ and R⁴ are independently straight- or branched-chain alkyl having 1 to 7 carbon atoms or alkoxy substituted straight- or branched-chain alkyl having 2 to 11 carbon atoms provided that R¹ is different than R³ when R² is the same as R⁴ and R¹ is different than R⁴ when R² is the same as R³.

2. An unsymmetrical azonitrile according to claim 1, which is

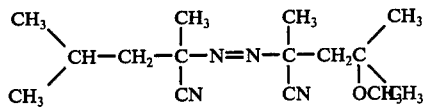

3. An unsymmetrical azonitrile according to claim 1, which is

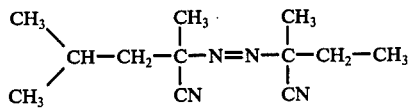

4. An unsymmetrical azonitrile according to claim 1, which is

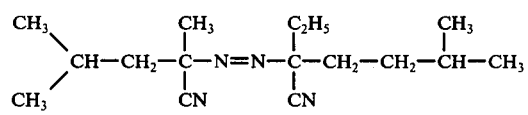

5. An unsymmetrical azonitrile according to claim 1, which is

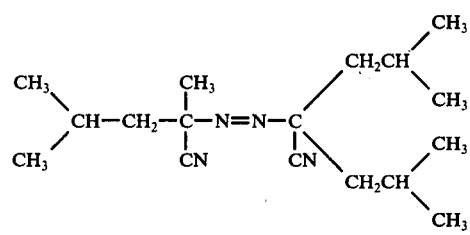

6. A composition containing an unsymmetrical azonitrile as claimed in claim 1 and symmetrical azonitriles of the formulas

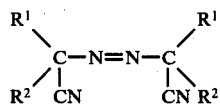

and

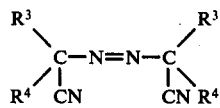

wherein $R^1$, $R^2$, $R^3$ and $R^4$ are independently straight- or branched-chain alkyl having 1 to 7 carbon atoms or alkoxy substituted straight- or branched-chain alkyl having 2 to 11 carbon atoms.

7. A composition according to claim 6, wherein the unsymmetrical azonitrile is 2-(1-cyano-1,3-dimethyl-butylazo)-4-methoxy-2,4-dimethyl-valeronitrile and the symmetrical azonitriles are 2,2'-azobis(2,4-dimethyl-valeronitrile) and 2,2'-azobis(4-methoxy-2,4dimethyl-valeronitrile).

* * * * *